United States Patent [19]

Wells et al.

[11] Patent Number: 4,512,163
[45] Date of Patent: Apr. 23, 1985

[54] INTEGRATED CARDIOPLEGIA DELIVERY SYSTEM

[75] Inventors: Edward S. Wells, Whitmore Lake; Spencer K. Ford, Dexter; Jack E. Werner, Ann Arbor; Erin J. Lindsay, Dexter, all of Mich.

[73] Assignee: Minnesota Mining and Manufacturing Company, Saint Paul, Minn.

[21] Appl. No.: 548,298

[22] Filed: Nov. 3, 1983

Related U.S. Application Data

[62] Division of Ser. No. 279,175, Jun. 30, 1981, Pat. No. 4,427,009.

[51] Int. Cl.³ .............................................. B67D 5/62
[52] U.S. Cl. ...................................... 62/394; 62/396; 62/434; 128/400; 165/108
[58] Field of Search .................... 62/394, 396, 434; 128/399, 400, DIG. 3; 165/108

[56] References Cited

U.S. PATENT DOCUMENTS

| | | | |
|---|---|---|---|
| 2,271,648 | 2/1942 | Kleist | 62/396 |
| 3,064,649 | 11/1962 | Fuson | 128/400 |
| 3,293,868 | 12/1966 | Gonzalez | 128/399 |
| 3,370,454 | 2/1968 | Flores | 165/108 |
| 3,504,674 | 4/1970 | Swenson et al. | 128/400 |
| 3,687,193 | 8/1972 | Wright | 62/394 |
| 3,699,776 | 10/1972 | La Raus | 62/394 |
| 3,927,980 | 12/1975 | Leonard | 422/48 |
| 3,941,356 | 3/1976 | Mason | 422/44 |
| 4,249,923 | 2/1981 | Walda | 62/394 |

OTHER PUBLICATIONS

"A Simple Method of Cold Coronary Perfusion," Hillel Lakes, M.D. et al., The Annals of Thoracic Surgery, vol. 25, No. 4, Apr. 1978.
"Cold Cardioplegia Versus Hypothermia for Myocardial Protection," The Journal of Thoracic and Cardiovascular Surgery, vol. 76, No. 5, Nov. 1978.

Primary Examiner—Ronald C. Capossela
Attorney, Agent, or Firm—Donald M. Sell; James A. Smith; Jennie G. Boeder

[57] ABSTRACT

A cardioplegia system in which cardioplegia medication or a mixture of arterial blood and medication is delivered to the heart of a patient undergoing open heart surgery. A cooling system incorporates flat coils vertically disposed in upright tanks in which the level of cooling liquid is controlled and thus the percentage area of the coil which is immersed. This permits the control of the cooling while isolating the blood or medication from the cooling system.

6 Claims, 10 Drawing Figures

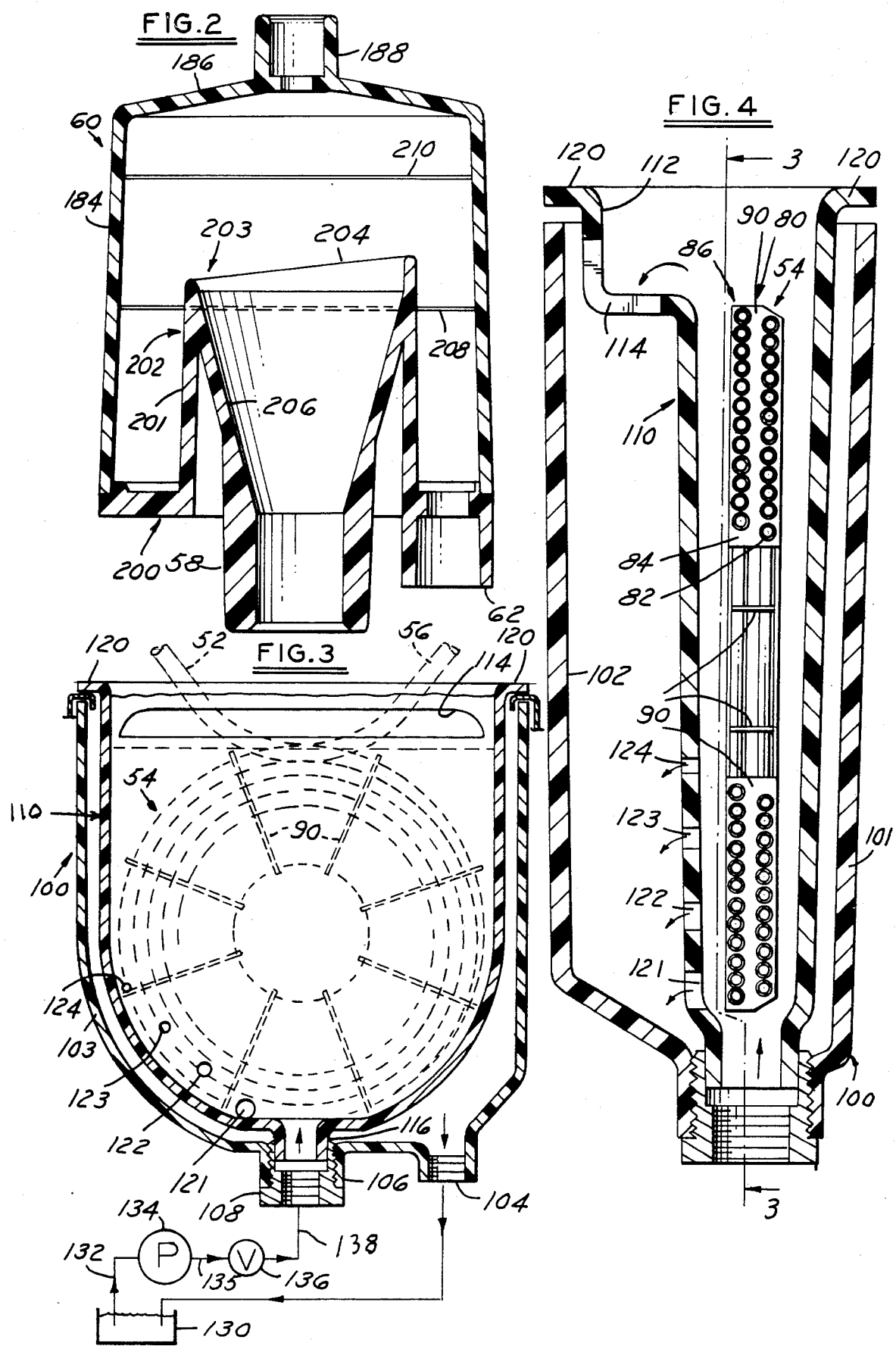

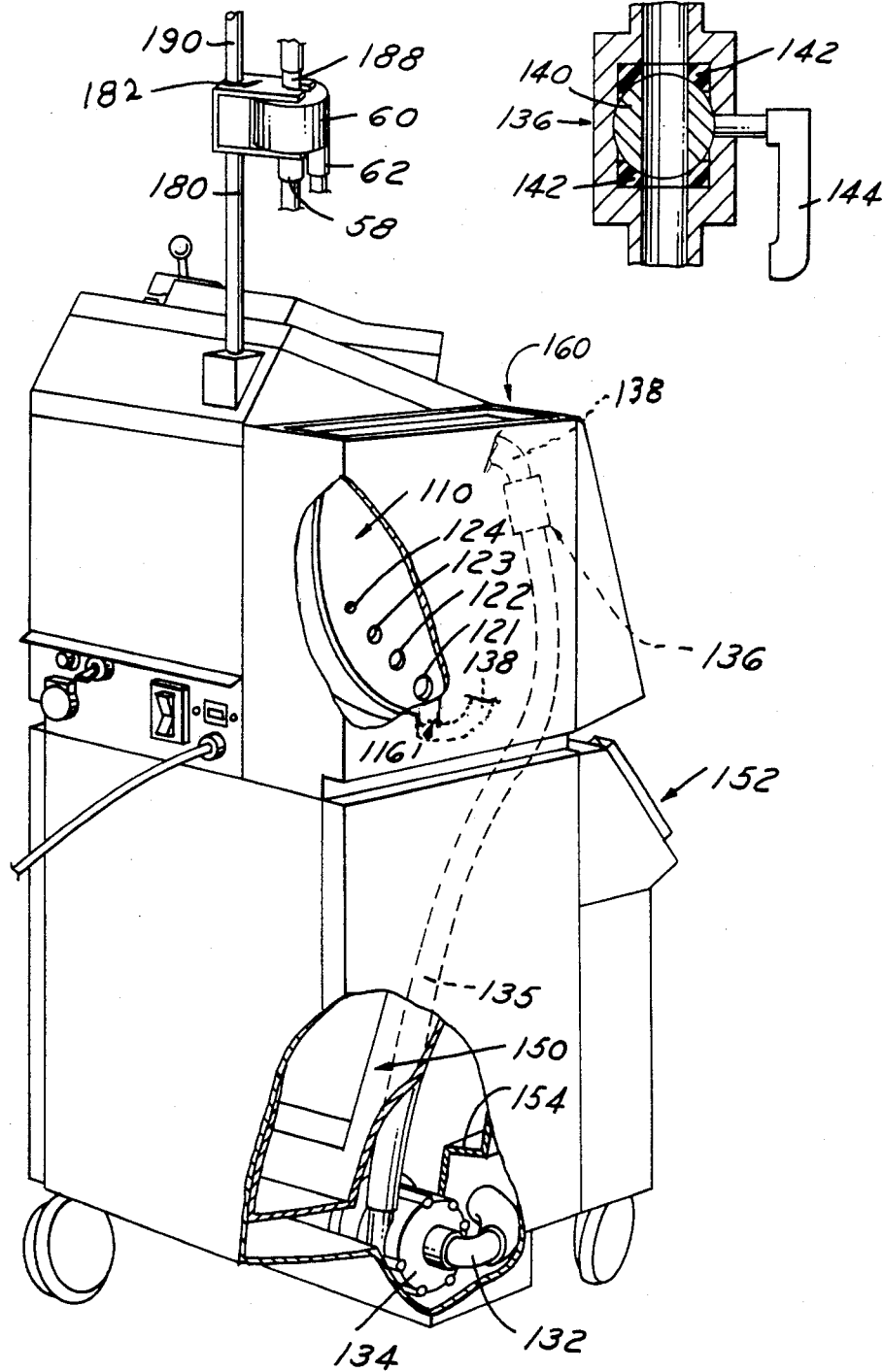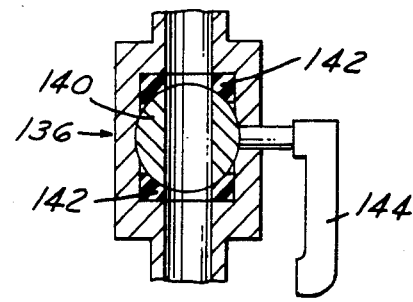

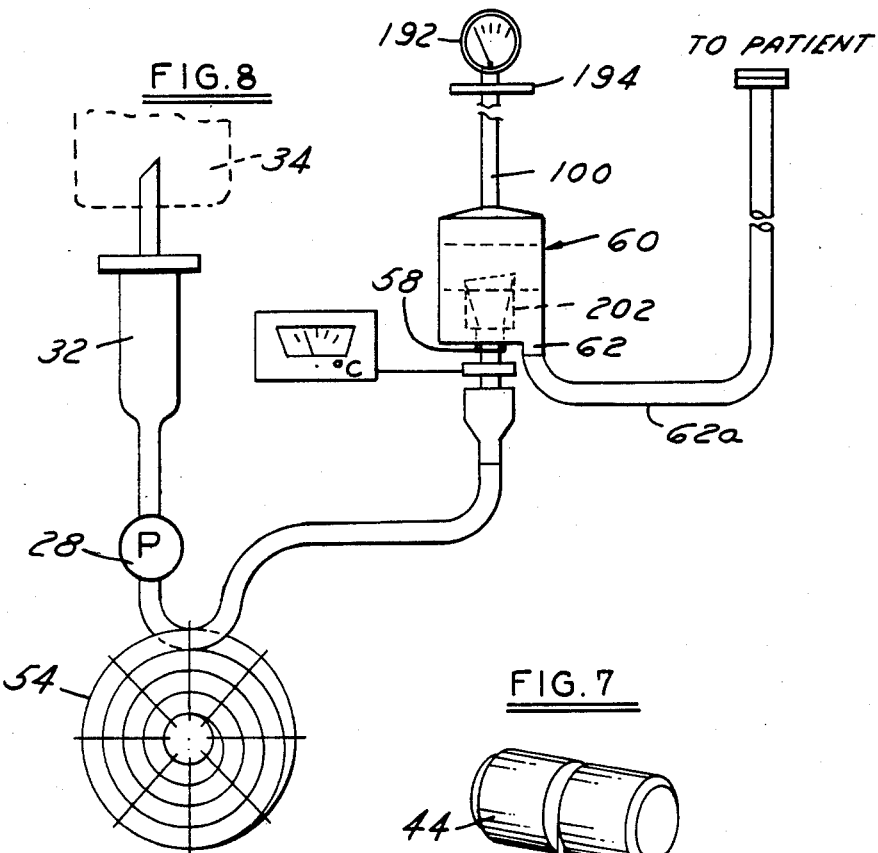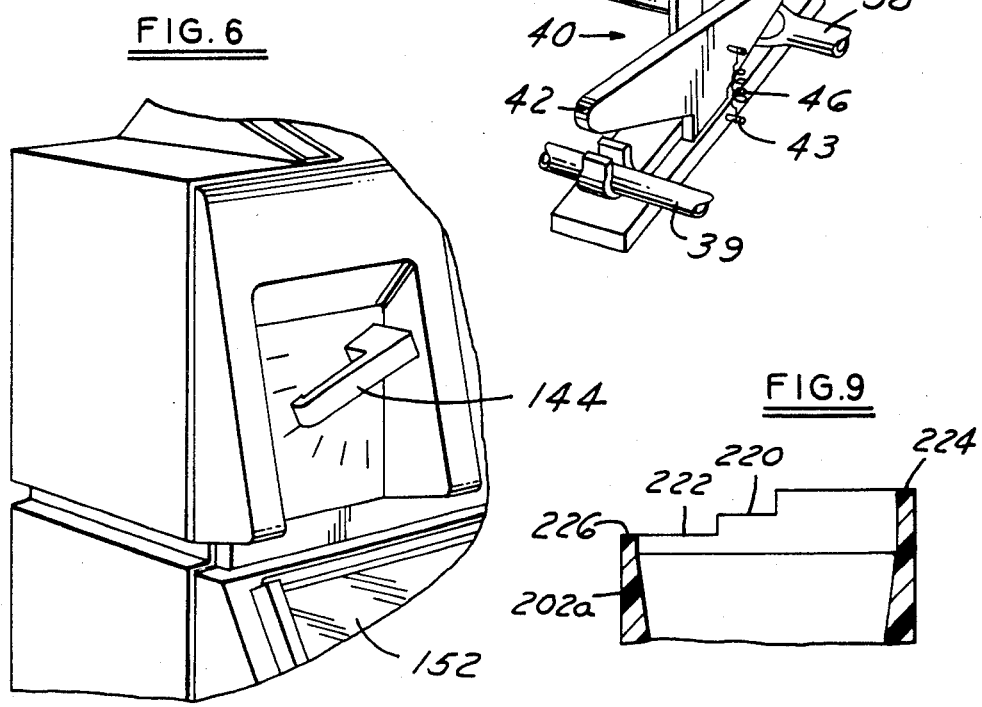

INTEGRATED CARDIOPLEGIA DELIVERY SYSTEM

This is a division of application Ser. No. 279,175 filed June 30, 1981, now U.S. Pat. No. 4,427,009.

FIELD OF INVENTION

Extracorporeal support systems for cardiovascular surgery and particularly methods and apparatus for cooling and administering drugs to the heart during open heart surgery to provide myocardial protection.

BACKGROUND OF THE INVENTION

Open heart surgery has been practiced for a number of years and the techniques for protection of the patient have been under study for all of this period. When the blood of the patient is by-passed to an extracorporeal support system which maintains the pumping function of the heart and the oxygenation function of the lungs, it is important that the heart itself be protected from ischemia, that is, deficiency of oxygenated blood in the heart muscles. In the circumstances of heart surgery, the possibility of damage to the heart is greatly reduced by cooling and administering drugs to the heart in a technique called "cardioplegia". A system for cooling the heart using the actual blood of the patient has also been developed and the use of blood as the vehicle for delivery of the cardioplegic solution has the advantage of keeping the heart oxygenated while it is arrested for the surgery.

Various methods for achieving cardioplegia have been used such as ice for slush baths with cooling coils submerged therein. Literature on the subject includes:

*A Simple Method of Cold Coronary Perfusion*, Hillel Lakes, M.D. et al The Annals of Thoracic Surgery, Vol. 25, No. 4, April 1978

*Cold Cardioplegia Versus Hypothermia for Myocardial Protection*, The Journal of Thoracic and Cardiovascular Surgery, Vol. 76, No. 5, November 1978

The present invention relates to an improved system for achieving cardioplegia which can be used in conjunction with the life support equipment in a combined plan making it easier to control and administer the cold oxygenated blood and/or drugs. In previous techniques, the batch system has been used in which a quantity of the patient's blood is mixed with a quantity of medication in a single batch and then introduced into the patient's heart. From time to time, new batches might be requested by the attending surgeon and prepared and administered.

It is an object to provide a cardioplegic system which is more readily controlled and monitored and which enables the administration of the solution in a continuous fashion if desired as distinguished from the batch system. A roller pump can be used to control and monitor the cardioplegia flow rate, and temperature monitoring is available at a location convenient to an operator. In addition, the administration of drugs along with the cold solution has more reliability and reproducibility in this system and apparatus to be disclosed and the mixing of the medication and blood can be achieved in a much more efficient manner than can be done in the batch system.

In the present invention, an improved cooling coil, cooling bath and control is disclosed wherein the area of heat transfer is controlled by liquid level which is determined by a suitable flow valve adjustment.

An object of this system is to utilize a continuous flow of a coolant and to adjust fluid levels in the cooling system to vary the area of contact of the cooling coil and thus the temperature to be achieved.

A further improvement lies in a bubble trap to minimize the possibility of air entering the aorta, this being associated with a temperature monitor, and serving also in connection with a pressure isolator and pressure monitoring and limiting system.

The transparent bubble trap is placed at a highly visible location for an operator and in normal operation will function to remove such few bubbles as occur in a fully primed system. If there is a line break or a drug bag empties, there is the possibility of air entering the system. This will cause a change in the solution level in the bubble trap although the trap will continue to function as intended. A continued drop in level will warn the operator to shut down the system long enough to isolate the difficulty and remedy the flow pattern.

Other objects and features of the invention will be apparent in the following description and claims in which the principles of the invention are set forth together with a detailed disclosure of the manner and process of using the invention directed to persons skilled in this art to enable the practice of the invention, all in connection with the best mode presently contemplated for the invention.

BRIEF DESCRIPTION OF THE DRAWINGS

DRAWINGS accompany the disclosure and the various views thereof may be briefly described as:

FIG. 2, a sectional view of the bubble trap element of the system.

FIG. 3, a side sectional view of the cooling coil assembly on line 3—3 of FIG. 4.

FIG. 4, a sectional view of the cooling coil assembly at 90° to the section of FIG. 3.

FIG. 5, a view of a mobile control unit illustrating the relative position of the cooling coil assembly.

FIG. 6, a view of the control unit and the coolant valve control.

FIG. 7, a view of a multiple tube control valve.

FIG. 8, a modified crystalloid cardioplegia system.

FIG. 9, a view of a modified blood well in the bubble trap.

FIG. 10, a sectional view of a ball valve control for ice water flow.

DETAILED DESCRIPTION OF THE INVENTION AND THE MANNER AND PROCESS OF USING IT

Figure 1:
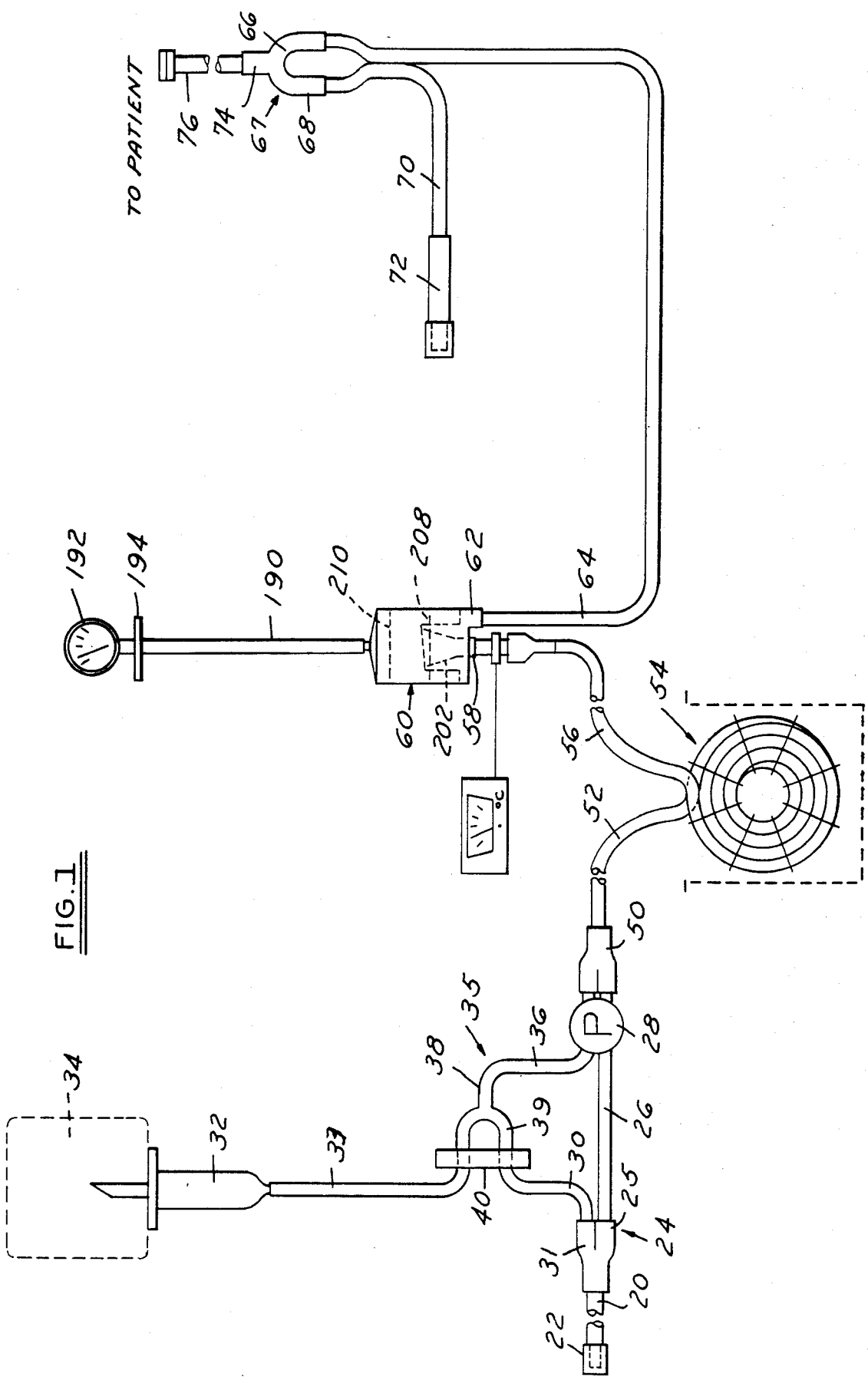
FIG. 1, a generalized view of a blood base cardioplegia system showing the various elements of the system.

Reference is made, first of all, to a copending application of Walter L. Carpenter and Bruce A. Amrine, Ser. No. 137,716, filed Apr. 7, 1980, wherein a Cardioplegia Delivery System is described now abandoned.

The Cardioplegia System in General

In FIG. 1 of the present disclosure, a proportioned blood cardioplegia system is illustrated wherein the tube 20, shown in the drawing with a temporary sealing cap 22, is to be connected to a source of oxygenated arterial blood and leads to a Y connection 24, one leg 25 of which connects through a tube 26 to a peristaltic roller pump 28. This pump is of the type generally described in DeVries U.S. Pat. No. 3,700,301, dated Oct.

24, 1972, but has a suitable race and guides for a double tube application.

A second tube 30 from leg 31 of the Y connection 24 leads to a leg 39 of a "Y" connection which joins also with a tube 33 connected to a drip chamber 32, above which is a drug bag or bottle 34. The tubes 30, 33 are looped at 35 to form the "Y" connection which joins with a tube 36 leading through the roller pump 28 in parallel with the tube 26. The legs 38, 39 of the loop 35 are controlled by a valve 40 which is movable to close one or the other of the legs selectively. A two-position valve of this nature is shown in FIG. 7 wherein a rocker bar 42 pivoted at 43 is actuated by a handle 44. The valve can be an overcenter type wherein a spring 46 serves to hold the valve in one position or the other to squeeze the tubes 38 and 39 selectively to a closed position. In the particular embodiment shown, the handle 44 lies in the direction of the tube which is occluded.

The tube portion 30 serves as a blood by-pass when leg 38 is occluded, thus preventing a suction collapse of tube 36 and possible degasification due to this suction.

The valve 40 is used to close by-pass tube 30 when medication is being fed through tubes 33, leg 38, and tube 36. When tube 33 is closed by valve 40, the by-pass is open.

Tubes 26 and 36 merge flow beyond pump 28 at a Y connection 50 into a tube 52 which constitutes an inlet end of a multiple-wind, flat coil 54 which has an outlet end 56 leading to the inlet 58 of a bubble trap and monitor housing 60. This housing 60 and the multiple-wind coil 54 will be described in detail below.

The housing 60 has an outlet 62 connected to a tube 64 leading to one leg 66 of a Y connector 67 which has a second leg 68 connected by a tube 70 which, in the system, is connected to a cardiotomy reservoir. A cap 72 closes tube 70 prior to the connection in the system. The stem 74 of Y 67 connects to a tube 76 leading to a cannula (not shown) which is inserted at a suitable location to perfuse the heart when an operation is in progress.

The Cooling System

Reference has been made generally in the description directed to FIG. 1, to the multiple-wind, flat coil 54. This coil is shown in greater detail in FIGS. 3 and 4. A single length of tubing having an end 52, for example, is wound from outside to inside in a flat coil 80 down to a central wind 82 leaving an opening, then crossed over to a second central wind 84 and wound outwardly in a flat coil 86 which has a tangential outlet end 56. Suitable thin radial stabilizer plates 90 properly apertured can be used to retain the coil in the wound and flat position. Thus, the wound coil can be handled as a unit and readily connected in the system. This coil is used to pass the solution of blood and/or drugs through a cooling medium, usually ice water, to cool the solution. The vertical flat coil is considered to be the best mode but the coil could also consist of vertical loops of a continuous tube or horizontal loops, or both, the runs of any of the coils extending through a predetermined vertical range in the cooling chamber in which it is disposed so that the coil can be immersed in cooling water at various heights to control the amount of heat transfer.

In FIGS. 3 and 4, an outer, upright cooling tank 100 with a relatively flat shape with an open top is illustrated having end walls 101 and 102 connected by a continuous side wall 103. An outlet opening 104 is provided at the lower corner as viewed in FIG. 3. Centrally, at the bottom, an inlet 106 is provided having a threaded nipple 108 extending therethrough.

An inner, upright cooling tank 110 again has spaced end walls forming a relatively flat narrow chamber with a flared top flange 112 provided with an elongate overflow slot 114. The lower portion of inner container 110 has a neck 116 which is received in sealing relation in the nipple 108. This provides an inlet for the inner container 110. The rounded bottom of the container adapts to the coil 54 which is supported vertically in the container, the coil ends 52 and 56 extending out of the open top. The top of container 110 has flanges 120 which can serve to stabilize the inner container within the outer container in conjunction with the telescoping fit of neck 116 in nipple 108.

The left-hand wall of the inner container 110 has a series of vertically spaced holes 121, 122, 123 and 124 graduated in size. As shown diagrammatically in FIG. 3, a tank 130 for holding ice water is connected through a suitable inlet pipe 132 to a pump 134 and thence through a conduit 135 to a manually adjustable valve 136 and a conduit 138 leading to inlet nipple 108.

The valve 136 can be a simple ball valve as shown in FIG. 10 with a ball 140 having a diametrical opening nested between sealing collars 142 and operated by a handle 144. Any suitable valve may be utilized, manually operable, or mechanized in a more elaborate set up.

A mobile control unit or console is shown in FIGS. 5 and 6. An ice water tank 150 in the bottom of the unit can be charged with ice through a door 152, and a sump 154 has the inlet tube 132 lying therein. The outlet tube 135 from the pump 134 leads to valve 136 shown diagrammatically, and from the valve the conduit 138 connects to the inner tank inlet 116 through nipple 108 (FIG. 3).

FIG. 6 shows the handle 144 of the ball valve which can be moved to graduated positions to control the amount of ice water flowing to the inner tank 110. The water to this tank will outflow through holes 121 to 124 and thus the level of water in the inner tank will influence the percentage of the coil 54 which is under the water level. The holes 121, 122, 123 and 124 are calibrated in size and location to linearize the graduated positions of the valve handle 144 to the depth of the cooling water in the inner tank. The size, shape and number of the holes can be varied to achieve the desired result. A single suitably shaped aperture can be utilized to achieve the desired overflow characteristic in conjunction with the valve adjustment characteristic to effect controllable temperatures with the coolant overflow.

The console has a top opening 160 which allows ready access to the tanks 103 and 110 so the coil 54 may be readily inserted and removed. The inner tank 110 can be lifted out of the outer tank for cleaning purposes and this provides access to the outer tank for the same purpose. The closed coil system prevents any contact of the ice water with the cardioplegic solution and the coil unit with the associated tubes and connectors is a disposable unit for one use only.

The Bubble Trap

Reference has been made to the bubble trap 60 shown in FIGS. 1, 2 and 5. On the console shown in FIG. 5 is a vertical support rod 180 with an adjustable support bracket 182 which supports the bubble trap shown in cross-section in FIG. 2. A domed, essentially cylindrical, transparent plastic housing 184 has an integral domed top 186 in the center of which is an outlet nipple 188 to which is attached a vertical pressure monitor tube 190 (FIG. 1). The tube 190 and a hydrophobic filter 194 at the top thereof is part of the disposable system. A pressure gauge 192 is mounted on tube 190 isolated by the filter. A transducer may be mounted in place of the gauge to have a digital readout on a console panel.

A base 200 seals the bottom of the cylinder 184, this base having an off-center outlet nipple 62 (FIG. 2). Centrally of the base is a cylindrical wall 201 forming a blood well 202, the wall 201 being spaced inwardly of the walls of the housing 184. The top of the well 202 has an angled rim 204 with a descending angle in a direction away from the location of the outlet 62.

The degree of angle can vary but, as one example, the maximum height of the well wall from the floor of the base 200 at the right of FIG. 2 is one (1) inch and the minimum height at the left is 0.9 inches. The inside diameter of the cylinder 184 can also vary but, as one example, the diameter is 1.60 inches while the outside diameter of the well 202 is 1.03 inches at the base and 1.0 inches at the top.

An inner wall 206 diverges from the well wall 201 and narrows to a blood inlet nipple 58. It will be noted that there are two etched lines 208 and 210 on the wall of cylinder 184. Line 208 is a minimum level indicator while line 210 is provided to indicate a normal blood level. The function of these lines will be described in connection with the operation of the device. As an alternate construction to that shown in FIG. 2, the top rim of the well 202 may be stepped rather than angled, as shown, for example, in FIG. 9 when the well 202a has descending steps 220 and 222 from the high point 224 to the low point 226.

The Operation of the Apparatus

The system shown in FIG. 1 is called a proportional system and the proportions may vary, but, as an example, the blood tube or conduit 30 is two times the diameter of the medication tube 36 to provide an area ratio of 4 to 1. Thus, when the tubes are passed through the same roller pump, there will be a proportional mixing of the material in the two tubes.

Ice and water are placed in the tank 150 so that pump 134 can circulate ice water through the tube 135 to the tank 110. The amount of water in tank 110 is controlled by valve 136 and control handle 144 so the level of ice water is raised around the coil 54 to a proper overflow level for a desired temperature of arterial blood or cardioplegia solution.

Tube 20 is connected to an arterial blood supply of a patient from an oxygenator and the roller pump 28 is started. Valve 40 will be in a position to close by-pass tube 30. Arterial blood mixed with suitable medication will pass through the coil 54 and be cooled after which it enters the bubble trap chamber through inlet 58. The blood will enter the well 202 through the entrance passage 206 and the operator can control the level of the blood to, for example, the level of line 210 (FIG. 2). Any bubbles will surface and rise to the top of the chamber 184 above the blood level. The pressure on the air chamber above the level is reflected in the gauge 192 or a suitable transducer. Blood, free of bubbles, will outflow at 62 to tube 64 and reach the Y connection 67. It will pass through tube 76 to a suitable cannula into the heart. Thus, the cooled blood together with the included medication will have a desired cardioplegic effect on the heart while an operation proceeds. Suitable closure clamps can divert blood to a cardiotomy reservoir from by-pass tube 70 if desired.

A suitable temperature monitoring site 59 in the form of a short section of stainless steel tube below the bubble trap inlet 58 is inserted in the line 56 so that an operator can adjust liquid level around coil 54 to a desired level to achieve desired cooling.

As bubbles rise to the surface of the blood in chamber 184, this will reflect in the level of the liquid in the trap. If blood level falls in the bubble trap, this may be an indication of a breakdown in the system either because of a dry medication bag or a leak upstream of the pump. As the level in the bubble trap falls, blood will pass over the lowest lip 203 (FIG. 2) at a point circumferentially furthermost remote from the blood outlet 62. Thus, this will provide the longest flow path for the blood in the bubble trap and give any air an increased opportunity to reach the blood surface before the blood enters the outlet leading to the patient. If the level in the bubble trap drops to a point below guideline 208, the system may be shut down momentarily to locate the source of the problem, and then restarted.

In FIG. 8, a crystalloid cardioplegia system is illustrated in which there is no mixing of the arterial blood with the nutrient or medication going to the heart. The pump 28 moves the material from supply 34 through the cooling coil 54, then to the bubble trap and through tube 62a to the patient. Other elements of this system are essentially the same as previously described with the exception that there is no recirculation line.

We claim:
1. A cooling system for cardioplegia and other uses which comprises:
    (a) a body of cooled liquid such as ice water,
    (b) a cooling tank to hold cooled liquid at varying levels in said tank,
    (c) a cooling coil for holding liquid to be cooled, said cooling coil supported in said tank and having inlet and outlet ends independent of said cooling tank,
    (d) means to move said cooled liquid to said tank, and
    (e) means to control the flow of cooled liquid to and from said tank to control the level of cooled liquid in said cooling tank and thus control the area of said cooling coil exposed to said cooled liquid.
2. A cooling system as defined in claim 1 in which said cooling tank comprises a relatively flat, upright tank open at the top, a cooling coil consisting of a plurality of loops disposed in said tank, the general shape of the coil being substantially flat and vertically disposed in said upright tank.
3. A cooling system as defined in claim 1 in which said means to control the flow of cooled liquid to said tank comprises a pump and a control valve to control the flow of cooled liquid from said pump to said cooling tank.
4. A cooling system for cardioplegia and other uses which comprises:
    (a) a body of cooled liquid such as ice water,
    (b) a cooling tank to hold cooled liquid at varying levels in said tank,
    (c) a cooling coil for holding liquid to be cooled, said cooling coil supported in said tank and having inlet and outlet ends independent of said cooling tank,
    (d) means to move said cooled liquid to said tank,
    (e) means to control the flow of cooled liquid to said tank, and

(f) a second tank which serves as a receptacle and discharge vessel for said cooling tank;

wherein said cooling tank has one or more openings to discharge said cooled liquid to said second tank at varying levels dependent on the rate of flow of cooled liquid to said cooling tank so as to control the level of cooled liquid in said cooling tank and thus control the area of said cooling coil exposed to said cooled liquid.

5. A cooling system as defined in claim 4 in which said cooling tank and second tank have a common inlet and are readily separable to facilitate cleaning of each of said tanks.

6. A cooling system as defined in claim 4 in which said cooling tank overflows at varying levels into said second tank and said second tank has a discharge outlet for said cooled liquid.

* * * * *